Figure 1:
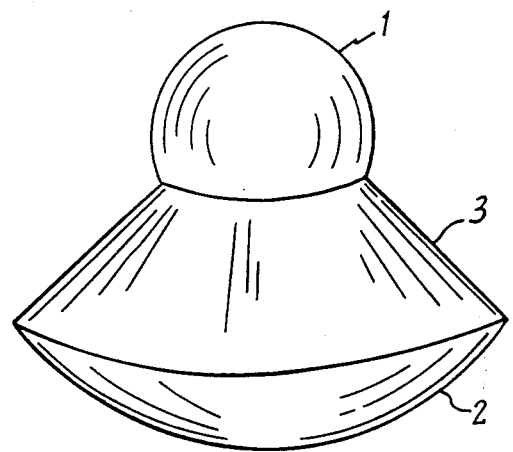

United States Patent [19]

Leclercq et al.

[11] Patent Number: 4,846,840
[45] Date of Patent: Jul. 11, 1989

[54] JOINT PROSTHESIS

[76] Inventors: Sylvain Leclercq, 1 rue du Régiment de la Chaudière, Bernieres sur Mer; Jacques Aubriot, 17 rue de l'Académie; Vincent Mercier, 6 rue des Cordeliers, both of 14000 Caen, all of France

[21] Appl. No.: 135,356

[22] Filed: Dec. 21, 1987

[51] Int. Cl.⁴ ............................................. A61F 2/32
[52] U.S. Cl. .................................... 623/23; 623/18
[58] Field of Search .................. 623/16, 18, 20, 21, 623/22, 23

[56] References Cited

U.S. PATENT DOCUMENTS

| 3,641,590 | 2/1972 | Michele | 623/22 |
| 3,916,451 | 4/1975 | Buechel et al. | 623/20 |
| 4,231,122 | 4/1980 | Koeneman | 623/20 |
| 4,695,282 | 9/1987 | Forte et al. | 623/22 |

FOREIGN PATENT DOCUMENTS

| 2247721 | 4/1974 | Fed. Rep. of Germany | 623/22 |
| 2534587 | 2/1976 | Fed. Rep. of Germany | . |
| 3101333 | 12/1985 | Fed. Rep. of Germany | 623/22 |
| 2061466 | 6/1971 | France | . |
| 2554342 | 5/1985 | France | 623/22 |
| 0426096 | 6/1967 | Switzerland | 623/22 |
| 1527498 | 10/1978 | United Kingdom | 623/22 |

Primary Examiner—Richard J. Apley
Assistant Examiner—David J. Isabella
Attorney, Agent, or Firm—Griffin, Branigan & Butler

[57] ABSTRACT

The joint prosthesis according to the invention is characterized in that it comprises two substantially concentric convex opposite surface portions (1, 2). Preferably the convex surface portions are portions of a sphere which are connected together by a frustoconical portion (3) and one (1) of the convex surface portions has a greater radius of curvature than the other (2).

7 Claims, 1 Drawing Sheet

JOINT PROSTHESIS

The present invention concerns a joint prothesis and more particularly but not exclusively a hip prosthesis.

A joint is formed by at least two joint or articular surfaces which are movable with respect to each other. The hip for example is formed on the one hand by the convex spherical femoral epiphysis and on the other hand the concave spherical cotyle. The necessity for a prosthesis may arise either as a result of deterioration of one of the two surfaces or deterioration of both. A distinction is made, among present hip prostheses, between two types of prosthesis: cups and prostheses with centro-diaphysial support.

Cups are aimed only at replacing pathological joint surfaces. The femoral surface and the cotyloidal surface can be replaced, or only one thereof. The cups may or may not be sealed. That type of prosthesis has the advantage of preserving the epiphysal tissue and in the event of wear or failure can be replaced by a prosthesis of the second type. The prosthesis is stable as it is of substantial diameter but that on the other hand assumes a more substantial amount of wear.

The second type of prosthesis comprises a prosthetic stem in the femoral diaphysis. The stem is supported on the diaphysial cortical portion. The articular portion is a sphere which can be articulated directly with the natural cotyle or with a prosthetic cotyle. In the latter case, it is possible and an attractive proposition to reduce the diameter of the sphere in order to reduce the amount of wear of the prosthesis but then there is a danger of instability and dislocation. In addition those prostheses assume more substantial resection of the bone shaft than in the case of cups so that in the event of wear or failure they can be replaced only by prostheses of the same type in the course of an operation which is often a long and difficult one.

Moreover, bone is a living tissue which is perpetually undergoing repair and alteration. Densification or in contrast resorption thereof depend on a number of factors among which mechanical stresses are the most important. Now, setting a joint prosthesis in position will interfere with the range of stresses transmitted in the boney tissue.

Four types of stresses are distinguished, in simplified form: shearing, traction, bending and compression. Compression stresses are those which best make it possible to achieve a bone response of high quality, provided that they retain a value which is close to the physiological value.

An aim of the present invention is to provide a joint prosthesis which favours transmission of the forces along natural lines and which favours compression forces for preserving or reconstituting the boney shaft.

In order to achieve that aim, the invention provides a joint prosthesis comprising two substantially concentric convex opposite surface portions.

Thus, the direction of the forces applied to the prosthesis passes through the centre thereof and respects the equilibrium of the joint. In addition transmission of the resultant force at the location of the joint interface is effected in a direction normal to the convex surface portions, which is generally in accordance with the direction of the natural lines in the bones which are connected by the joint.

In accordance with an advantageous embodiment of the invention, the convex surface portions are portions of a sphere. That provides for easy sliding movement of the prosthesis in the cavities into which it is inserted.

In accordance with another advantageous aspect of the invention one of the convex surface portions has a radius of curvature which is greater than the other. That promotes the sliding movement on one of the parts of the joint.

In accordance with a preferred embodiment of the invention which is associated with a prosthesis comprising convex surface portions having different radii of curvature, the convex surface portions are connected to each other by a frustoconical portion. That provides for maximum deflection movement of the joint about the convex surface portion with the smallest radius of curvature. In accordance with yet another particular aspect of the invention the prosthesis comprises two rigid elements which are connected by an elastic member, each of the rigid elements carrying one of the convex surfaces. The elastic member thus forms a damper between the two bones which are in association with each other by virtue of the prosthesis.

Figure 2:
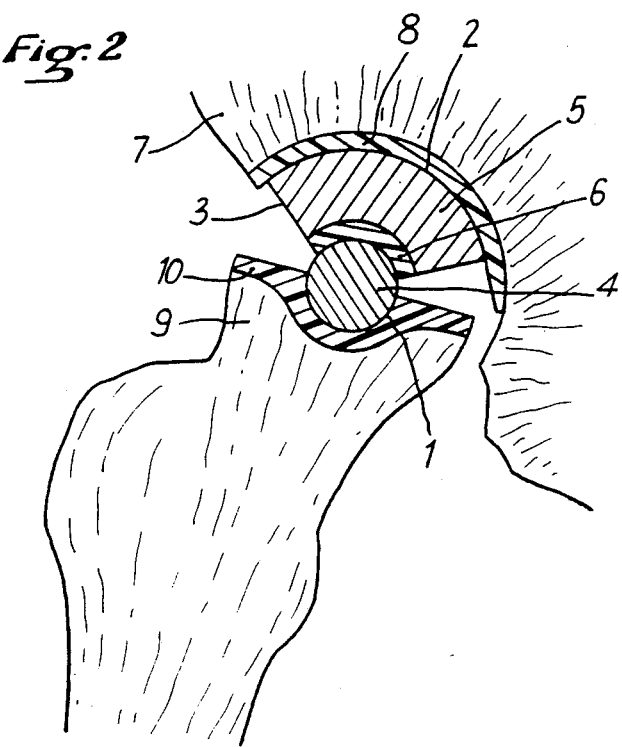

Other features and advantages of the invention will be apparent from the following description with reference to the accompanying drawing in which:

FIG. 1 is an elevational view of an embodiment of a prosthesis according to the invention, and FIG. 2 is a sectional view of a hip joint fitted with a prosthesis according to the invention.

Referring to the drawing, the joint prosthesis according to the invention comprises a first convex surface portion 1, for example a portion of a sphere, associated with an oppositely disposed concentric convex surface portion 2, for example a second portion of a sphere, having a radius of curvature which is greater than that of the first portion of a sphere 1, by way of a frustoconical surface portion 3. In the embodiment shown in FIG. 1, the prosthesis is made in one piece, for example stainless steel.

FIG. 2 shows application of the prosthesis according to the invention to a hip joint shown in section in a plane passing substantially through the axis of the femur. In that embodiment, the first convex surface 1 is the outside surface of the ball of steel as indicated at 4 while the second opposite convex surface 2 is formed by the outside surface of a hollow ball portion which is connected to the ball 4 by an elastic member 6, for example a portion of polyethylene or elastomer which is glued to the ball 4 and the portion 5.

In the illustrated use, the pelvic bone 7 has been slightly hollowed out and a cup 8 has been implanted in the femoral cotyle. Moreover the head 9 has been sectioned along a plane passing through the centre of the head and normal to the axis of the lines of force of the femoral neck. The stump of the bone has then been hollowed out to fit a femoral cup 10.

The diameter of the surface 2 of largest radius is preferably disposed in the cotyloidal cup while the small-diameter surface 1 is preferably fitted into the fermoral cup. In order to minimise the frictional forces, it is preferable for the small-diameter surface 1 to be of a radius which is as small as possible, while however being compatible with the pressure stresses transmitted by the prosthesis. In turn, the large-diameter surface is preferably to be a little larger than the diameter of the head of the femur in order to permit deflection of the prosthesis in the cotyloidal cup 8 in the event that the upper surface of the femoral cup 10 should come into contact with the frustoconical wall portion 3. For a human hip joint which is 49 mm in diameter, it is suggested that a large diameter of about 50 mm and a small diameter of about 22 mm should be adopted. The cups may be made of different materials, the thickness of which will depend on the joint in which the prosthesis is fitted and the material chosen. For a hip joint, cups made of polyethylene may advantageously be of a thickness of from 6 to 8 mm.

It is noted that in the embodiment illustrated the concentric character of all the elements and all the surfaces of the different components make it possible to eliminate any mechanical torque. There is therefore no flexural or traction stress at the location of the prosthesis implantation interfaces and reconstitution of the boney tissue at the location of the interface with the cups is therefore very markedly promoted.

In addition all the stresses applied to the prosthesis are compression forces which pass through the centre of the prosthesis. Static equilibrium of the prosthesis is therefore permanent. Mobilisation occurs naturally over the small-diameter couple. The risk of dislocation is limited by the mobility of the large-diameter couple. Finally, implantation of that prosthesis saves on the boney shaft, which permits replacement in the event of wear or failure by a prosthesis involving centro-diaphysial support.

It will be appreciated that the invention is not limited to the embodiment described and alternative forms thereof are possible without departing from the scope of protection. In particular, although the particular embodiment illustrated comprises two spherical convex surfaces, convex surfaces of other shapes, for example a parabolic shape, may be used, it being appreciated that the associated cups are of a complementary shape permitting for example a rolling movement with sliding motion over a portion of the movement of the prosthesis. Likewise, although the embodiment described comprises precisely concentric convex surfaces, it is also possible to provide convex surfaces which are slightly off-centered, in particular for joints such as the shoulder. Finally, if the state of the coyle permits, the prosthesis can be mounted directly in the existing cotyle, without the provision of a prosthetic cotyle.

Preferably, the centre of the prosthesis coincides with the centre of the femur head or, inthe case of another joint, with the centre of the epiphysis which is replaced by the prosthesis.

In short, the precise form of the prosthesis, its dimension and the materials to be used depend on the joint in question and will be adapted to each particular case to take account of the morphology of each individual.

We claim:

1. A hip joint prosthesis adapted for disposition between the pelvic bone and the femoral head of a hip joint, comprising:
    (1) a first convex surface portion adapted for rotatable disposition in a cavity formed in the femoral head;
    (2) a second convex surface portion adapted for rotatable disposition in a cvity formed in the pelvic bone and which is convex in a direction opposite to the convex direction of the said first convex surface portion;
    (3) a third portion disposed between and immovably affixed to said first and second convex surface portions;
    and wherein the radius of curvature of the first convex surface portion is smaller than that of the second convex surface portion.

2. The device of claim 1 wherein both said convex surface portions are portions of a sphere.

3. The device of claim 2 wherein the said third portion has a configuration in the shape of a conical frustrum.

4. The device of claim 3 wherein the base of the frustrum is fixedly attached to said second convex surface portion.

5. The device of claim 1 wherein the first convex surface portion is disposed in said cavity by positioning said first convex surface portion in a cup means which is configured on one surface thereof to fit with a cavity formed in the femoral head and configured on the opposite surface thereof to the shape of said first convex surface.

6. The device of claim 1 wherein the second convex surface portion is disposed in said cavity by positioning said second convex surface in a cup means which is configured on one surface thereof to fit with a cavity formed in the pelvic bone.

7. The device according to claim 1 wherein an elastic member is disposed between the first convex surface and the said third portion and said first convex portion and said third portion are fixedly attached to said elastic member.

* * * * *